United States Patent [19]

Howarth et al.

[11] Patent Number: 4,571,392
[45] Date of Patent: Feb. 18, 1986

[54] 6-SUBSTITUTED DERIVATIVES OF CLAVULANIC ACID

[75] Inventors: Thomas T. Howarth, Reigate; King Luk, Cranleigh, both of England

[73] Assignee: Beecham Group Limited, England

[21] Appl. No.: 370,081

[22] Filed: Apr. 20, 1982

Related U.S. Application Data

[63] Continuation of Ser. No. 907,570, May 19, 1978, abandoned.

[30] Foreign Application Priority Data

May 19, 1977 [GB] United Kingdom ............... 21022/77

[51] Int. Cl.[4] ............... C07D 448/04; A61K 31/42
[52] U.S. Cl. ............... 514/210; 260/245.3
[58] Field of Search ............... 424/272; 260/245.3

[56] References Cited

U.S. PATENT DOCUMENTS

| | | | |
|---|---|---|---|
| 4,076,826 | 2/1977 | Christenson et al. | 424/272 |
| 4,088,656 | 5/1978 | Howarth et al. | 260/245.3 |
| 4,093,626 | 6/1978 | Hunt | 260/245.3 |
| 4,315,006 | 2/1982 | Storer | 424/250 |
| 4,315,935 | 2/1982 | Ali | 424/258 |
| 4,316,907 | 2/1982 | Oxford et al. | 549/60 |
| 4,317,826 | 3/1982 | Gleason | 424/258 |
| 4,317,835 | 3/1982 | Van Dijk et al. | 424/309 |
| 4,321,254 | 3/1982 | Ali | 424/40 |
| 4,341,786 | 7/1982 | Demarinis et al. | 424/258 |
| 4,350,685 | 9/1982 | Ali et al. | 424/45 |
| 4,351,842 | 9/1982 | Coles | 424/274 |
| 4,352,809 | 10/1982 | Bondinell et al. | 424/258 |
| 4,366,167 | 12/1982 | Corbett | 424/274 |
| 4,379,787 | 4/1983 | Lunn et al. | 424/246 |
| 4,382,084 | 5/1983 | Ponsford et al. | 424/114 |
| 4,382,932 | 5/1983 | Lunn et al. | 424/246 |
| 4,385,047 | 5/1983 | Ali | 424/43 |
| 4,388,316 | 6/1983 | Lunn et al. | 424/246 |
| 4,393,072 | 7/1983 | Merkel et al. | 424/275 |
| 4,395,406 | 7/1983 | Gacek et al. | 424/180 |
| 4,395,421 | 7/1983 | Taylor et al. | 424/283 |
| 4,396,619 | 8/1983 | Lunn et al. | 424/246 |
| 4,396,620 | 8/1983 | Lunn | 424/246 |
| 4,397,845 | 8/1983 | Allen | 424/180 |
| 4,399,142 | 8/1983 | Durant et al. | 424/258 |
| 4,401,665 | 8/1983 | Sheinaus et al. | 424/233 |
| 4,401,668 | 8/1983 | Lunn | 424/246 |
| 4,402,949 | 9/1983 | Hartmann et al. | 424/183 |
| 4,402,955 | 9/1983 | Lunn | 424/246 |
| 4,402,974 | 9/1983 | Matier et al. | 424/308 |
| 4,402,976 | 9/1983 | Muir | 424/311 |
| 4,405,596 | 9/1983 | Helbig et al. | 424/33 |
| 4,406,898 | 9/1983 | Lunn et al. | 424/246 |
| 4,406,899 | 9/1983 | Aburaki et al. | 424/246 |
| 4,411,907 | 10/1983 | Toia | 424/273 B |
| 4,411,909 | 10/1983 | Gonella | 424/275 |
| 4,414,204 | 11/1983 | Tarcsay et al. | 424/177 |
| 4,421,760 | 12/1983 | Box | 424/274 |
| 4,427,690 | 1/1984 | Cole et al. | 424/272 |
| 4,428,958 | 1/1984 | Ponsford | 424/272 |
| 4,444,754 | 4/1984 | Stirling et al. | 424/114 |
| 4,444,783 | 4/1984 | Eglington | 424/114 |
| 4,446,146 | 5/1984 | Southgate et al. | 424/274 |

FOREIGN PATENT DOCUMENTS 827926 10/1975 Belgium.

Primary Examiner—Mark L. Berch
Attorney, Agent, or Firm—Jacobs & Jacobs

[57] ABSTRACT

The present invention provides the compounds of the formula (II):

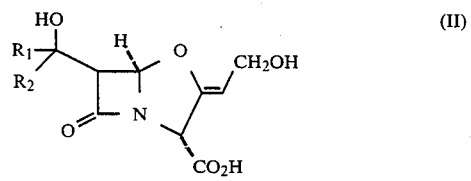

and salts and esters thereof wherein $R_1$ is a hydrogen atom or an alkyl group of 1–4 carbon atoms and $R_2$ is a hydrogen atom or an alkyl group of 1–4 carbon atoms or is joined to $R_1$ to form part of a 5-, 6- or 7 membered carbocyclic ring. These compounds are $\beta$-lactamase inhibitors able to enhance the effectiveness of pencillins and cephalosporins. Their preparation and compositions containing them are described.

30 Claims, No Drawings

6-SUBSTITUTED DERIVATIVES OF CLAVULANIC ACID

CROSS-REFERENCE

This is a continuation, of Ser. No. 907,570, filed May 19, 1978, now abandoned.

The present invention relates to β-lactam containing β-lactamase inhibitors, to the process for their preparation and to compositions containing them.

Belgian Pat. No. 827926 discloses clavulanic acid of the formula (I):

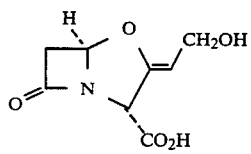

(I)

and its salts and esters are β-lactamase inhibitors which enhance the effectiveness of penicillins and cephalosporins against β-lactamase producing bacteria. It has now been found that substitution at C-6 produces a new class of β-lactamase inhibitors which may be used to enhance the effectiveness of penicillins and cephalosporins, for example against β-lactamase producing strains of *Staphylococcus aureus*.

The present invention provides the compounds of the formula (II):

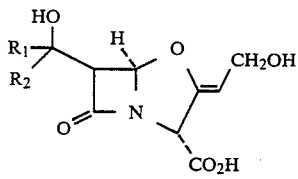

(II)

and salts and esters thereof wherein $R_1$ is a hydrogen atom or an alkyl group of 1–4 carbon atoms and $R_2$ is a hydrogen atom or an alkyl group of 1–4 carbon atoms or is joined to $R_1$ to form part of a 5-, 6- or 7-membered carbocyclic ring.

Suitably $R_1$ is a hydrogen atom or a methyl, ethyl, n-propyl or n-butyl group. Suitably $R_2$ is a hydrogen atom or a methyl, ethyl, n-propyl or n-butyl group.

Most suitably $R_1$ is a hydrogen atom or a methyl group.

Most suitably $R_2$ is a hydrogen atom or a methyl group.

One preferred group of compounds of this invention include those wherein $R_1$ is a hydrogen atom. Thus preferred compounds of this invention include those of the formula (III)

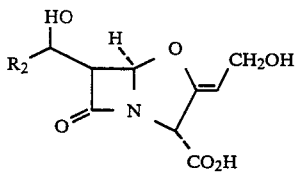

(III)

and salts and esters thereof wherein $R_2$ is a hydrogen atom or an alkyl group of 1–4 carbon atoms. In these compounds $R_2$ is more suitably a hydrogen atom or a methyl, ethyl, n-propyl or n-butyl group. Most suitably $R_2$ in these compounds is an ethyl group.

The compounds of this invention may have cis- or trans-configuration at the β-lactam ring as shown in formulae (IV) and (V):

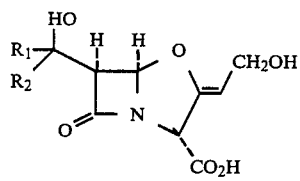

(IV)

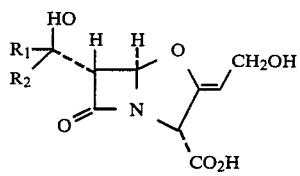

(V)

If desired mixtures of the compounds of the formulae (IV) and (V) or their salts or esters may be used as synergists though it is more suitable to employ a single isomer, for example a compound of the formula (V) or its salt or ester or more preferably a compound of the formula (IV) or its salt or ester.

Suitable salts of the compounds of this invention include the lithium, sodium, potassium, calcium, barium, magnesium, ammonium, trimethylammonium, triethylammonium, pyridinium or the like salts. Particularly suitable salts of this invention include the lithium, sodium, calcium and potassium salts. The sodium and potassium salts are prefered pharmaceutically acceptable salts.

Suitable esters of this invention include those of the formula (VI) and (VII):

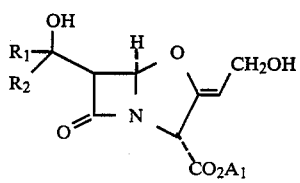

(VI)

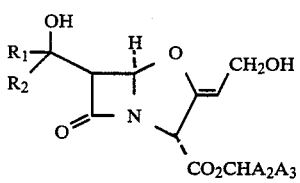

(VII)

wherein $A_1$ is an alkyl group of 1–6 carbon atoms optionally substituted by an alkoxyl or acyloxyl group of 1–7 carbon $A_2$ is an alkenyl group of up to 5 carbon atoms or is a phenyl group optionally substituted by a fluorine, chlorine, bromine, nitro or alkyl or alkoxyl of up to 4 carbon atoms; and $A_3$ is a hydrogen atom, an alkyl group of up to 4 carbon atoms or a phenyl group optionally substituted by a fluorine, chlorine, bromine, nitro or alkyl or alkoxyl of up to 4 carbon atoms.

Certain favoured groups $A_1$ include the methyl, methoxymethyl, acetoxymethyl, acetoxyethyl, phthalidyl, ethoxycarbonyloxymethyl, α-ethoxycarbonyloxyethyl and the like groups.

Particularly suitable esters of the formula (VI) include those wherein $A_1$ is a methyl, methoxymethyl or like readily base hydrolysable group.

Particularly suitable esters of the formula (VII) include those wherein $CHA_2A_3$ is a benzyl, p-methoxybenzyl or like readily hydrogenolysable group.

Favoured groups $R_1$ and $R_2$ for inclusion in the compounds of formulae (IV), (V), (VI) and (VII) are those referred to in relation to formulae (II) and (III).

The carbocyclic ring previous referred to in relation to formula II is cyclopentyl, cyclohexyl and cycloheptyl rings.

The present invention provides a process for the preparation of the compounds of the formula (II) as hereinbefore defined which process comprises the reaction of a compound of the formula (VIII):

$$R_1-CO-R_2 \qquad \text{(VIII)}$$

wherein $R_1$ and $R_2$ are as defined in relation to formula (II) with a trianion derived from the corresponding ester of clavulanic acid and three equivalents of a strong base of low nucleophilicity and thereafter quenching the resulting reaction mixture with a proton source and thereafter if desired converting the resulting ester of the compound of the formula (II) into the compound of the formula (II) or its salt.

The reaction of the compound of the formula (VIII) with the trianion of the ester of clavulanic acid will normally take place at a low temperature, for example $-80°$ to $-40°$ C. and more suitably at about $-70°$ C. in an inert aprotic solvent such as tetrahydrofuran, dioxane, hexamethylphosphoramide or mixtures of such solvents. Since the trianion is a highly reactive species it is desirable to carry out the reaction under a dry, inert gas such as argon or nitrogen.

Once the reaction of the compound of the formula (VIII) and the trianion has taken place the resulting ion may be quenched by the addition of six equivalents of an acid such as hydrochloric acid. It is desirable that the addition of the acid also takes place at a depressed temperature.

The trianion may be represented by the formula (IX):

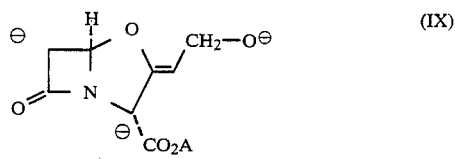

wherein A is a group such that $CO_2A$ is an ester group.

The trianion is normally generated and utilized in situ. Thus most suitably the trianion is prepared at a depressed temperature, for example $-80°$ C. to $-40°$ C. and preferably $-70°$ C. in a dry aprotic solvent such as tetrahydrofuran, dioxane, hexamethylphosphoramide or mixtures thereof under an inert gas such as argon or nitrogen. The base used to generate the trianion will be a strong base of low nucleophilicity such as a lithium dialkylamide, for example lithium di-isopropylamide or equivalent agents.

The ester of the compound of the formula (II) may be extracted from the reaction mixture by allowing the mixture to warm to room temperature, diluting with brine, optionally adding a further water immiscible organic solvent, separating the phases, drying the organic phase and evaporating it at low pressure. Any acid of the formula (II) in the organic layer may be extracted into water at pH 7.5 and later esterified and combined with the ester obtained in the organic extract. The resulting ester may be purified chromatographically if desired, for example using a conventional support such as silica gel and a conventional eluant such as cyclohexane-ethyl acetate. The desired fractions may be identified by tlc using silica covered plates and ethyl acetate/cyclohexane (1/1) with potassium permanganate spray for identification. The cis- and trans-isomers are separable on such systems.

The esters of the compounds of the formula (II) may be converted into the corresponding compound of the formula (II) or its salts by the methods known to be suitable for deesterification of esters of clavulanic acid (eg. as in Belgian Pat. No: 847045). Accordingly this invention provides a process for preparing a compound of the formula (II) as hereinbefore described or a salt thereof which process comprises the hydrolysis or hydrogenolysis of a hydrolysable or hydrogenolysable ester of a compound of the formula (II).

Particularly suitable methods of producing salts of the compounds of the formula (II) include mild base hydrolysis of the corresponding methyl, methoxymethyl or like ester or hydrogenolysis using a palladium catalyst of the corresponding benzyl, p-methoxybenzyl or like ester optionally in the presence of a base such as $Li_2CO_3$, $NaHCO_3$, $KHCO_3$, $CaCO_3$ or the like.

The salts of the compounds of the formula (II) may also be prepared by neutralisation of the corresponding acid of the formula (II). This may be conveniently carried out on a solution of the acid produced by the hydrogenation of a hydrogenolysable ester. Suitable bases for neutralisation include carbonates, bicarbonates and hydroxides particularly lithium hydroxide since the lithium salts of the compounds of this invention have generally good stabilities. The said lithium salts may be converted into corresponding sodium, potassium or like pharmaceutically acceptable salts by conventional methods of ion exchange, for example by using an ion exchange resin in the form of the required salting ion.

The present invention also provides pharmaceutical compositions which comprise a compound of this invention and a pharmaceutically acceptable carrier.

The compositions of the invention include those in a form adapted for oral, topical or parenteral use and may be used for the treatment of infections in mammals including humans.

Suitable forms of the compositions of this invention include tablets, capsules, creams, syrups, suspensions, solutions, reconstitutable powders and sterile forms suitable for injection or infusion. Some compositions may contain conventional pharmaceutically acceptable materials such as diluents, binders, colours, flavours, preservatives, disintegrants and the like in accordance with conventional pharmaceutical practice in the manner well understood by those skilled in the art of formulating antibiotics.

Injectable or infusable compositions of salts of a compound of the formula (II) are particularly suitable as high tissue levels of a compound of the formula (II) can occur after administration by injection or infusion. Thus, one preferred composition aspect of this invention comprises a salt of a compound of the formula (II) in sterile form.

Unit dose compositions comprising a compound of the formula (II) or a salt or ester thereof adapted for oral administration form a further preferred composition aspect of this invention.

The compound of the formula (II) or its salt or ester may be present in the composition as sole therapeutic agent or it may be present together with other therapeutic agents such as a β-lactam antibiotic. Suitable β-lactam antibiotics for inclusion in the compositions of this invention include benzylpenicillin, phenoxymethylpenicillin, carbenicillin, azidocillin, propicillin, ampicillin, amoxycillin, epicillin, ticarcillin, cyclacillin, cefatriazine, pirbenicillin, α-sulphonyloxybenzylpenicillin, cephaloridine, cephalothin, cefazolin, cephalexin, cephacetrile, cephamandole nafate, cephapirin, cephradine, 4-hydroxy-cephalexin, cefaparole, cephaloglycine, and other well known penicillins, and cephalosporins or pro-drugs therefor such as hetacillin, metampicillin, 4-acetoxyampicillin, the acetoxymethyl, ethoxycarbonyloxymethyl, pivaloyloxymethyl or phthalidyl esters of benzylpenicillin or ampicillin, or the phenyl or indanyl α-esters of carbenicillin or ticarcillin or the like. Such compounds are frequently used in the form of a salt or hydrate.

Naturally if the penicillin or cephalosporin present in the composition is not suitable for oral administration then the composition will be adapted for parenteral administration.

When present together with a cephalosporin or penicillin, the ratio of a compound of the formula (II) or its salt or ester present to the other antibacterial agent may vary over a wide range of ratios, for example 3:1 to 1:10 and advantageously may be from 1:1 to 1:8, for example, 1:2, 1:3, 1:4, 1:5 or 1:6.

The total quantity of compound of the formula (II) in any unit dosage form will normally be between 25 and 1000 mg and will usually be between 50 and 500 mg, for example about 62.5, 100, 125, 150, 200 or 250 mg.

Compositions of this invention may be used for the treatment of infections on, inter alia, the respiratory tract, the urinary tract and soft tissues and mastitis in cattle.

Normally between 50 and 1000 mg of the compounds of the invention will be administered each day of treatment but more usually between 100 and 750 mg of the compounds of the invention will be administered per day, for example as 1–6 doses, more usually 2–4 doses.

The penicillin or cephalosporin in synergistic compositions of this invention will normally be present up to or at approximately the amount at which it is conventionally used.

Certain favoured compositions of this invention will contain from 150–1000 mg of amoxycillin, ampicillin or a pro-drug therefor and from 25–500 mg of a compound of the formula (II) or ester thereof and more suitably from 200–750 mg of amoxycillin or a salt thereof and from 50–250 mg of a compound of the formula (II).

The materials present in such compositions may be hydrated if required, for example ampicillin trihydrate or amoxycillin trihydrate may be employed. The weights of the antibiotics in such compositions are expressed on the basis of the weight of pro-drug.

Certain preferred compositions of this invention comprise a compound of this invention together with a cephalosporin. Particularly useful compounds of the invention for inclusion in such compositions include the pharmaceutically acceptable salts of the compounds of the formulae (II) or (III) such as the sodium or potassium salts. Certain favoured cephalosporins include cefazoline and cephaloridine.

The compounds of this invention preferred for use in the synergistic compositions of this invention are those having the cis-configuration about the β-lactam ring, that is a compound of the formula (IV) or a salt or ester thereof. Similarly, compounds within formula (III) are preferably of the cis-stereochemistry.

The following examples illustrate the invention.

EXAMPLE 1 p-Methoxybenzyl 6α-(1-methyl-1-hydroxyethyl)clavulanate

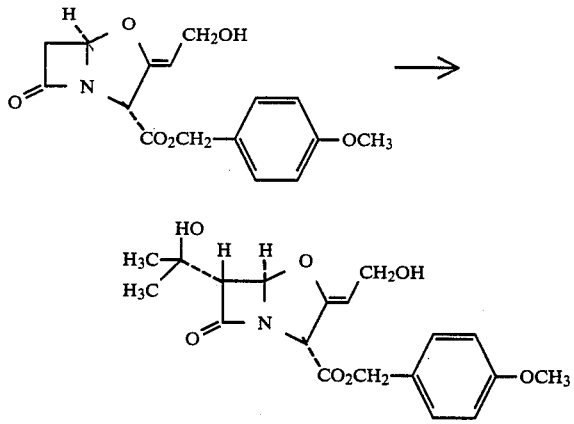

A solution of methyllithium in ether (2M, 15 ml) was added to a solution of diisopropylamine (0.03 mole, 4.2 ml) in tetrahydrofuran (20 ml) and hexamethylphosphoramide (5 ml) at −10° under Argon. The mixture was stirred at −10° for 15 min and then cooled to −70°. A solution of p-methoxybenzyl clavulanate (0.01 mole, 3.19 g) in tetrahydrofuran (10 ml) was added and the mixture was stirred at −70° for 5 min when solution was completed. Acetone (0.01 mole, 0.74 ml) was then added and the mixture was stirred at −70° for 5 min. The reaction was quenched with aqueous hydrochloric acid (5M, 10 ml) and then allowed to reach room temperature. Brine (40 ml) was added and the organic layer separated. The aqueous layer was washed with ethyl acetate (2×50 ml) and the combined organic extract was dried over anhydrous magnesium sulphate-sodium carbonate and then evaporated to give an oil. This was chromatographed over silica gel (25 g) and elution of the column with cyclohexane-ethyl acetate afforded the starting material (0.16 g) and p-methoxybenzyl 6α-(1-methyl-1-hydroxyethyl)clavulanate (0.07 g) as an oil, $[\alpha]_D^{20}$ +24.0° (c, 1.0; CHCl$_3$), $\nu_{max}$(CHCl$_3$) 1800, 1750, 1695, 1305, 1250, 1175, 1015, and 825 cm$^{-1}$, δ(CDCl$_3$), 7.23 (2H, d, J=9 Hz, ArH), 6.83 (2H, d, J=9 Hz, ArH), 5.61 (1H, s, 5—CH), 5.09 (2H, s, —CH$_2$Ar), 5.00 (1H, broad s, 3—CH), 4.80, (1H, broad t, J=8 Hz, 8—CH), 4.14 (2H, d, J=8 Hz, 9—CH$_2$), 3.77 (3H, s, —OCH$_3$), 3.21 (1H, s, 6—CH), and 1.38 (6H, s, —CH$_3$), m/e 319 (5, M$^+$—Me$_2$CO) and 121 (100).

EXAMPLE 2

Lithium 6α-(1-methyl-1-hydroxyethyl)clavulanic

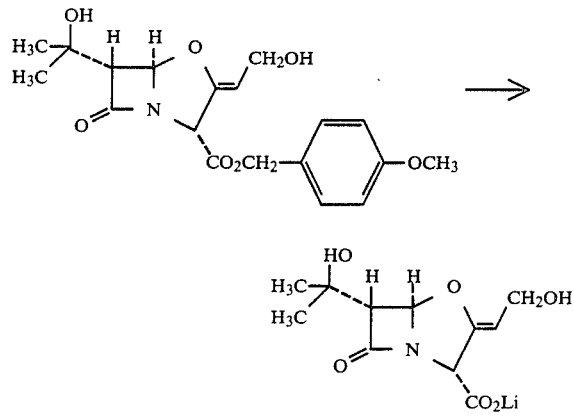

A solution of p-methoxybenzyl 6α-(1-methyl-1-hydroxyethyl)clavulanate (0.05 g) in tetrahydrofuran (9 ml) and water (2 drops) was hydrogenated at room temperature and atmospheric pressure in the presence of 10% palladium-charcoal (0.02 g) for 0.5 h. The reaction mixture was filtered and the filtrate diluted with water (10 ml) and titrated with aqueous lithium hydroxide solution (1M) to pH 7.5. The neutral solution was evaporated to dryness to give lithium 6α-(1-methyl-1-hydroxyethyl)clavulanate (0.025 g), $v_{max}$ (KBr) 1780, 1700, 1620, 1320, 1040, and 905 cm$^{-1}$, $\delta(D_2O)$ 5.63 (1H, s, 5—C$\underline{H}$), 4.89 (1H, s, 3—C$\underline{H}$), 4.87 (1H, broad t, J=8 Hz, 8—C$\underline{H}$), 4.10 (2H, d, J=8 Hz, 9—C$\underline{H}_2$), 3.38 (1H, s, 6—C$\underline{H}$), and 1.32 (6H, s, —C$\underline{H}_3$).

A strain of *Staphylococcus aureus* Russel not inhibited by the presence of 500 μg/ml of ampicillin alone was inhibited by 25 μg/ml of ampicillin in the presence of 5 μg/ml of the compound of this example.

EXAMPLE 3 p-Methoxybenzyl 6-(1-hydroxyethyl)clavulanate

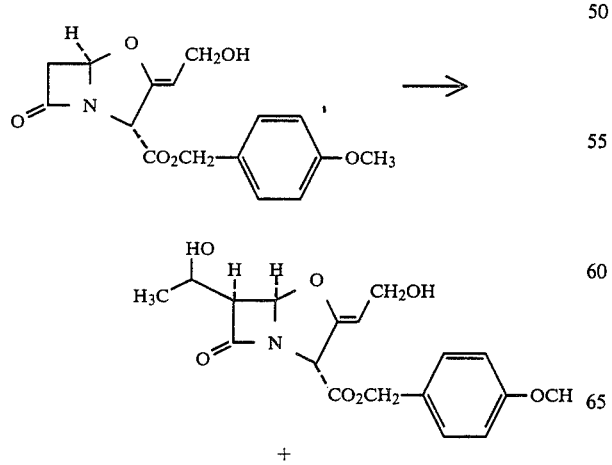

+

-continued

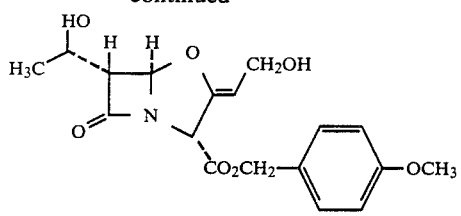

A solution of methyllithium in ether (2M, 37.8 ml) was added to a solution of diisopropylamine (10.58 ml) in tetrahydrofuran (30 ml) and hexamethylphosphoramide (7.5 ml) at −10° under Argon. The mixture was stirred at −10° for 15 min and then cooled to −70°. A solution of p-methoxybenzyl clavulanate (6.38 g) in tetrahydrofuran (10 ml) was added and the mixture was stirred at −70° for 5 min when solution was almost completed. Acetaldehyde (2 ml) was then added and the mixture was stirred at −70° for 5 min. The reaction was quenched with aqueous hydrochloric acid (5M, 26 ml) and then allowed to reach room temperature. Brine (100 ml) was added and the organic layer separated. The aqueous layer was washed with ethyl acetate (2×70 ml) and the combined organic extract was dried over anhydrous magnesium sulphate-sodium carbonate and then evaporated to give an oil. This was chromatographed over silica gel (30 g) and elution of the column with cyclohexane-ethyl acetate gave three fractions, A (0.62 g), B (0.26 g), and C (0.12 g), in order of increasing polarity. Fraction A was the starting material (n.m.r. and t.l.c. comparisions). Fraction B was rechromatographed over silica gel (10 g) and elution of the column with chloroform-methanol (9:1) gave p-methoxybenzyl 6α-(1-hydroxyethyl)clavulanate (0.09 g), $v_{max}$ (CHCl$_3$) 1800, 1750, 1700, 1310, 1175, 1040, and 850 cm$^{-1}$. $\delta$(CDCl$_3$) 7.21 (2H, d, J=9 Hz, Ar$\underline{H}$), 6.82 (2H, d, J=9 Hz, Ar$\underline{H}$), 5.62, 5.58 (1H, s, 5—C$\underline{H}$), 5.08 (2H, s, —CH$_2$Ar), 5.00 (1H, s, 3—C$\underline{H}$), 4.80 (1H, t, J=8 Hz, 8—C$\underline{H}$), 4.20 (1H, m, CH$_3$C$\underline{H}$OH), 4.14 (2H, d, J=8 Hz, 9—C$\underline{H}_2$), 3.76 (3H, s, OC$\underline{H}_3$) 3.24 (1H, m, 6—C$\underline{H}$), and 1.34 (3H, d, J=7 Hz, CH—C$\underline{H}_3$). Fraction C was further purified in the same way to give p-methoxybenzyl 6β-(1-hydroxyethyl)clavulanate (0.05 g), $v_{max}$ (CHCl$_3$), 1800, 1750, 1700, 1305, 1180, 1140, 1040, and 830 cm$^{-1}$, $\delta$(CDCl$_3$) 7.21 (2H, d, J=9 Hz, Ar$\underline{H}$), 6.83 (2H, d, J=9 Hz, Ar$\underline{H}$), 5.65 (1H, m, 5—C$\underline{H}$), 5.08 (2H, s, —CH$_2$Ar), 5.00 (1H, s, 3—C$\underline{H}$), 4.80 (1H, t, J=8 Hz, 8—C$\underline{H}$), 4.00-4.30

(3H, m, 9-C$\underline{H}_2$ and CH$_3$C$\underline{H}$—OH), 3.77 (3H, s, OC$\underline{H}_3$), 3.48 (1H, m, 6—C$\underline{H}$), and 1.30

(3H, d, J = 7Hz, C$\underline{H}_3$—CHOH).

EXAMPLE 4

Lithium 6α-(1-hydroxyethyl)clavulanate

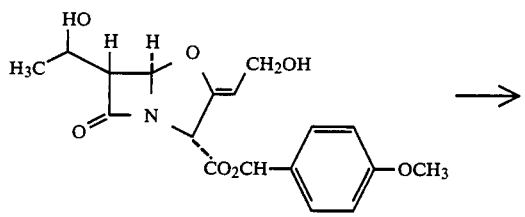

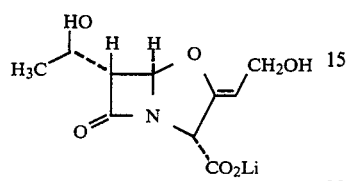

A solution of p-methoxybenzyl 6α-(1-hydroxyethyl)-clavulanate (0.08 g) in tetrahydrofuran (10 ml) and water (1 ml) was hydrogenated at room temperature and atmospheric pressure in the presence of 10% palladium-charcoal (0.04 g) for 0.5 h. The reaction mixture was filtered and the filtrate diluted with water (10 ml) and titrated with aqueous lithium hydroxide solution (1M) to pH 7.5. The neutral solution was evaporated to dryness to give lithium 6α-(1-hydroxyethyl)clavulanate (0.04 g), $\upsilon_{max}$ (KBr) 1780, 1695, 1620, 1310, 1140, 1040, and 900 cm$^{-}$, δ(D$_2$O) 5.57, 5.62 (1H, s, 5—C$\underline{H}$), 4.88 (1H, s, 3—C$\underline{H}$), 4.87 (1H, t, J=8 Hz, 8—C$\underline{H}$), 4.18 (1H, d, CH$_3$C$\underline{H}$OH), 4.10 (2H, d, J=8 Hz, 9OC$\underline{H}_2$), 3.38 (1H, m, 6—C$\underline{H}$), and 1.26

(3H, d, J = 7Hz, C$\underline{H}_3$CHOH).

EXAMPLE 5

Lithium 6β-(1-hydroxyethyl)clavulanate

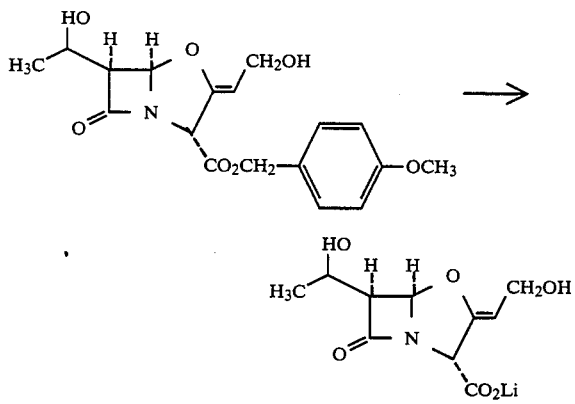

A solution of p-methoxybenzyl 6β-(1-hydroxyethyl)-clavulanate (0.04 g) in tetrahydrofuran (10 ml) and water (1 drop) was hydrogenated at room temperature and atmospheric pressure in the presence of 10% palladium-charcoal (0.02 g) for 0.5 h. The reaction mixture was filtered and the filtrate diluted with water (10 ml) and titrated with aqueous lithium hydroxide solution (1M) to pH 7.5. The neutral solution was evaporated to dryness to give lithium 6β-(1-hydroxyethyl)clavulanate (0.02 g), $\upsilon_{max}$ (KBr) 1780, 1700, 1620, 1310, 1140, and 900 cm$^{-1}$, δ(D$_2$O) 5.65 (1H, m, 5—C$\underline{H}$), 4.89 (1H, t, J=8 Hz, 3—C$\underline{H}$), 4.85 (1H, s, 3—C$\underline{H}$), 4.18 (1H, m, CH$_3$C$\underline{H}$—OH), 4.09 (2H, d, J=8 Hz, 9—C$\underline{H}_2$), 3.65 (1H, m, 6—C$\underline{H}$), and 3.26

(3H, d, J = 7Hz, C$\underline{H}_3$C$\underline{H}$—OH).

A strain of *Staphylococcus aureus* Russel not inhibited by the presence of 500 μg/ml was inhibited by 12.5 μg/ml of ampicillin in the presence of 1 μg/ml of the compound of this Example.

The compound of this Example was found to inhibit the β-lactamase from Enterobacter P99 (I$_{50}$<0.04 μg/ml), Proteus C889 (I$_{50}$ 0.28 μg/ml), *E.coli* JT4 (I$_{50}$ 0.23 μg/ml), and *Staphylococcus aureus* Russel (I$_{50}$ 5.4 μg/ml).

A strain of *E.coli* (JT410) not inhibited by 500 μg/ml of cephaloridine was inhibited by 4 μg/ml of the compound of this example.

EXAMPLE 6 p-Methoxybenzyl 6-(1-hydroxypropyl)clavulanate

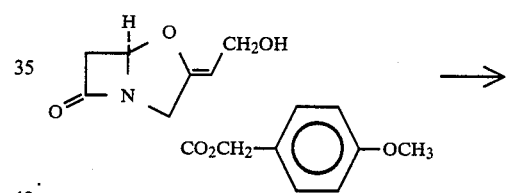

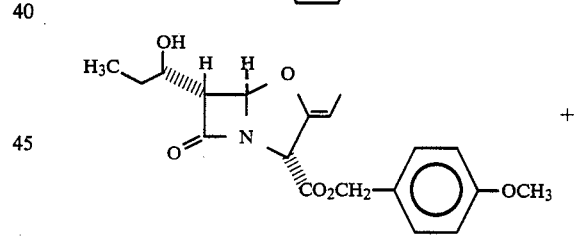

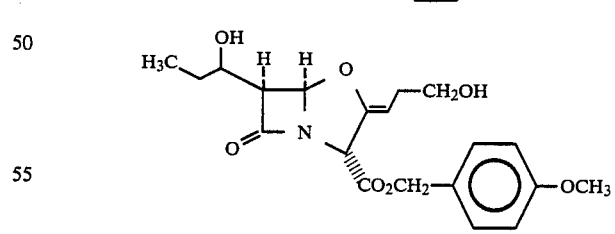

A solution of methyllithium in ether (2M, 16 ml) was added to a solution of hexamethyldisilazane (5.8 g) in tetrahydrofuran (40 ml) and hexamethylphosphoramide (10 ml) at −10° under Argon. The mixture was stirred at −10° for 15 minutes and then cooled to −70°. A solution of p-methoxybenzyl clavulanate (3.19 g) in tetrahydrofuran (10 ml) was added and the mixture was stirred at −70° for 5 minutes. Propanal (0.86 ml) in tetrahydrofuran (10 ml) was added dropwise over 5 minutes and the mixture was quenched with aqueous hydrochloric acid (5M, 13 ml) and brine (50 ml) and allowed to come to room temperature. The organic layer was separated and the aqueous layer extracted with ethyl acetate (2×50 ml). The combined organic extract was dried and evaporated to give an oil which was chromatographed over silica gel (100 g). Elution of the column with cyclohexane-ethyl acetate gave the starting material (0.14 g), p-methoxybenzyl 6α-(1-hydroxypropyl)clavulanate (0.04 g) as a mixture of two 6α-isomers, νmax (CHCl$_3$) 1800, 1750, 1700, 1310, 1250, 1180 and 1040 cm$^{-1}$, δ(CDCl$_3$) 0.97 (3H, t, J=8 Hz, —CH$_2$CH$_3$), 1.62 (2H, m, CHCH$_2$CH$_3$), 3.30 (1H, m, 6—CH), 3.75 (3H, s, OCH$_3$), 3.88 (1H, m, Et CHOH), 4.13 (2H, d, J=8 Hz, 9—CH$_2$), 4.79 (1H, broad t, J=8 Hz, 8—CH), 4.99 (1H, broad s, 3—CH), 5.06 (2H, s, —CH$_2$Ar), 5.58, 5.62 (1H, s, 5—CH), 6.80 (2H, d, J=9 Hz, ArH), and 7.20 (2H, d, J=9 Hz, ArH), m/e (relative intensity) 138(15), 137(5), 131(5), and 121(100), and p-methoxybenzyl 6β-(1-hydroxypropyl)clavulanate (0.16 g) as a mixture of two 6β-isomers, νmax (CHCl$_3$) 1800, 1750, 1700, 1305, 1250, 1175, and 1040 cm$^{-1}$, δ(CDCl$_3$) 0.93 (3H, t, J=7.5 Hz, —CH$_2$CH$_3$), 1.68 (2H, m, —CHCH$_2$CH$_3$), 3.40 (1H, m, 6—CH), 3.74 (3H, s, OCH$_3$), 3.89 (1H, m, EtCH—OH), 4.12 (2H, m, 9—CH$_2$), 4.87 (1H, broad t, J=8 Hz, 8—CH), 4.98 (1H, broad s, 3—CH), 5.05 (2H, s, —CH$_2$Ar), 4.69, 5.01 (1H, d, J=2.5 Hz, 5—CH), 6.79 (2H, d, J=9 Hz, ArH) and 7.18 (2H, d, J=9 Hz, ArH).

EXAMPLE 7

Lithium 6β-(1-hydroxypropyl)clavulanate

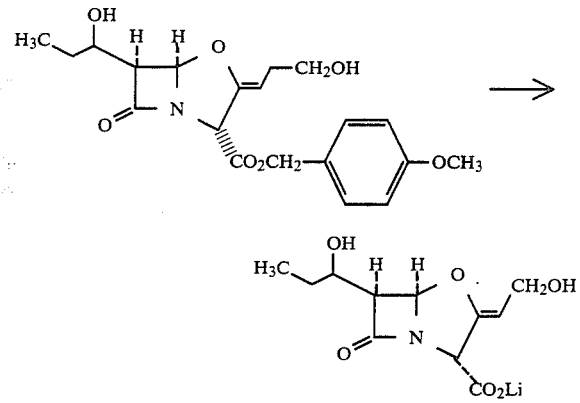

A solution of p-methoxybenzyl 6β-(1-hydroxypropyl)clavulanate (0.16 g) in tetrahydrofuran (20 ml) and water (1 drop) was hydrogenated at room temperature and pressure in the presence of 10% palladium-barium sulphate (0.2 g) for 0.5 hours. The reaction mixture was filtered and the filtrate diluted with water (15 ml) and neutralised with aqueous lithium hydroxide solution (1 ml) to pH 7.5. The solution was then evaporated to give, after trituration with ether, the title compound (0.1 g) as a solid, νmax (KBr) 1780, 1690, 1620, and 1310 cm$^{-1}$, δ(D$_2$O) 0.86 (3H, t, J=7.5 Hz, —CH$_2$CH$_3$), 1.36-1.73 (2H, m, —CHCH$_2$CH$_3$), 3.43-3.70 (1H, m, 6—CH), 3.64-3.97 (1H, m, EtCH —OH), 4.10 (2H, d, J=8 Hz, 9—CH$_2$), 4.84 (1H, broad s, 3—CH), 4.86 (1H, broad t, J=8 Hz, 8—CH), and 5.63 (1H, m, 5—CH).

The above compound was found to inhibit β-lactamase from Enterobacter P99 (I$_{50}$ 0.18 μg/ml), Proteus C889 (0.6 μg/ml), E.coli JT4 (0.18 μg/ml) and Staphylococcus aureus Russell (1.8 μg/ml).

The MIC of ampicillin against Staphyloccocus aureus Russel was reduced from 125 μg/ml to 1.5 μg/ml in the presence of 1 μg/ml of the compound of this example.

EXAMPLE 8

Lithium 6α-(1-Hydroxypropyl)clavulanate

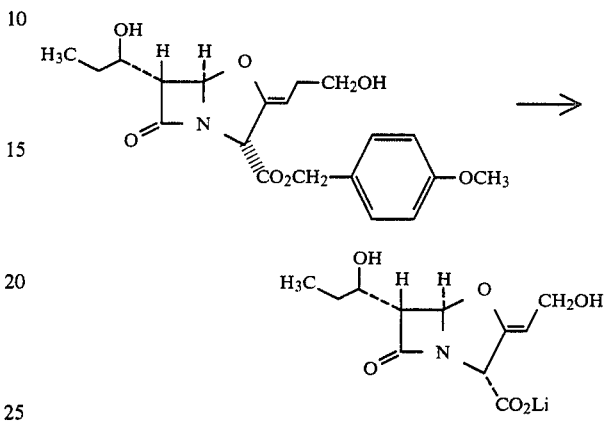

A solution of p-methoxybenzyl 6α-(1-hydroxypropyl)clavulanate (0.04 g) in tetrahydrofuran (10 ml) and water (1 drop) was hydrogenated at room temperature and pressure in the presence of 10% palladium-barium sulphate (0.04 g) for 0.5 hours. The reaction mixture was filtered and the filtrate diluted with water (10 ml) and neutralised with aqueous lithium solution (1 ml) to pH 7.5. The solution was then evaporated to give, after trituration with ether, the title compound (0.02 g) as a solid, νmax 1780, 1690, 1620 and 1310 cm$^{-1}$, δ(D$_2$O) 0.84 (3H, t, J=7.5 Hz, —CH$_2$CH$_3$), 1.37-1.84 (2H, m, —CHCH$_2$CH$_3$), 3.41 (1H, m, 6—CH), 3.53-3.93 (1H, m, EtCH—OH), 4.08 (2H, d, J=8 Hz, 9—CH$_2$), 4.81 (1H, broad t, J=8 Hz, 8—CH), 4.83 (1H, broad s, 3—CH), and 5.54, 5.59 (1H, s, 5—CH).

The above compound was found to inhibit β-lactamase from Enterobacter P99 (I$_{50}$ 1.2 μg/ml), Proteus C889 (I$_{50}$ 0.6 μg/ml), E.coli JT4 (I$_{50}$ 0.4 μg/ml) and Staphylococcus aureus Russell (I$_{50}$ 1.0 μg/ml).

The MIC of ampicillin against Staphyloccocus aureus Russel was reduced from 125 μg/ml to 1.5 μg/ml in the presence of 1.0 μg/ml of the compound of this example.

What we claim is:

1. A compound of the formula (II):

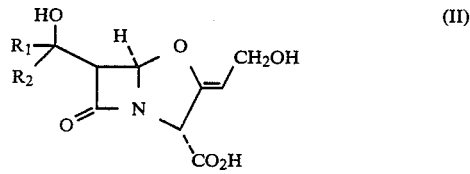

(II)

or a pharmaceutically acceptable salt thereof, wherein R$_1$ is hydrogen and R$_2$ is ethyl.

2. A compound according to claim 1 which has the cis-configuration at the β-lactam ring.

3. A compound according to claim 1 which has the trans-configuration at the β-lactam ring.

4. A compound according to claim 1 in the form of a pharmaceutically acceptable salt.

5. A compound according to claim 1 in the form of a sodium, potassium, calcium, barium, magnesium, ammonium, trimethylammonium, triethylammonium or pyridinium salt.

6. A compound according to claim 1 in the form of a sodium, potassium or calcium salt.

7. A compound according to claim 1 in the form of a sodium or potssium salt.

8. The lithium salt of a compound of the formula (II):

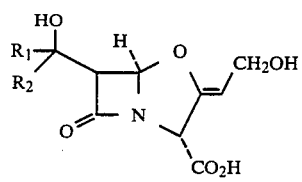

wherein $R_1$ is hydrogen and $R_2$ is ethyl.

9. The compound according to claim 8 which is lithium 6α-(1-hydroxypropyl clavulanate).

10. The compound according to claim 8 which is lithium 6β-(1-hydroxypropyl clavulanate).

11. A pharmaceutical composition useful for effecting β-lactamase inhibition in humans and animals which comprises β-lactamase inhibitory amount of a compound of the formula (II):

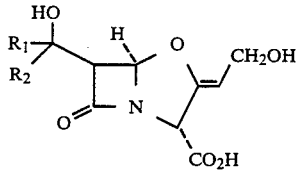

or a pharmaceutically acceptable salt thereof wherein $R_1$ is hydrogen and $R_2$ is ethyl, in combination with a pharmaceutically acceptable carrier.

12. A composition according to claim 11 wherein the compound has the cis-configuration at the β-lactam ring.

13. A composition according to claim 11 wherein the compound has the trans-configuration at the β-lactam ring.

14. A composition according to claim 11 wherein the compound is in the form of a pharmaceutically acceptable salt.

15. A composition according to claim 11 wherein the compound is in the form of a sodium, potassium, calcium, barium, magnesium, ammonium, trimethylammonium, triethylammonium or pyridinium salt.

16. A composition according to claim 11 wherein the compound is in the form of a sodium, potassium or calcium salt.

17. A composition according to claim 11 wherein the compound is in the form of a sodium or potassium salt.

18. A composition according to claim 11 in oral administration form.

19. A composition according to claim 11 in parenteral administration form.

20. A composition according to claim 11 in topical application form.

21. A method of effecting β-lactamase inhibition in humans and animals which comprises administering to human or animal in need thereof a β-lactamase inhibitory amount of a compound of the formula (II):

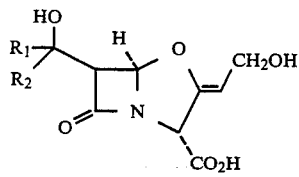

or a pharmaceutically acceptable salt thereof, wherein $R_1$ is hydrogen and $R_2$ is ethyl, in combination with a pharmaceutically acceptable carrier.

22. A method according to claim 21 wherein the compound has the cis-configuration at the β-lactam ring.

23. A method according to claim 21 wherein the compound has the trans-configuration at the β-lactam ring.

24. A method according to claim 21 wherein the compound is in the form of a pharmaceutically acceptable salt.

25. A method according to claim 21 wherein the compound is in the form of a sodium, potassium, calcium, barium, magnesium, ammonium, trimethylammonium, triethylammonium or pyridinium salt.

26. A method according to claim 21 wherein the compound is in the form of a sodium, potassium or calcium salt.

27. A method according to claim 21 wherein the compound is in the form of a sodium or potassium salt.

28. A method according to claim 21 wherein the administration is oral.

29. A method according to claim 21 wherein the administration is parenteral.

30. A method according to claim 21 wherein the administration is by topical application.

* * * * *